US011185716B2

(12) United States Patent
Liu et al.

(10) Patent No.: US 11,185,716 B2
(45) Date of Patent: Nov. 30, 2021

(54) CRANIAL IMMOBILIZATION APPARATUS FOR RADIATION THERAPY (71) Applicant: MEDICAL INTELLIGENCE MEDIZINTECHNIK GMBH, Schwabmuenchen (DE)

(72) Inventors: Rui Liu, Augsburg (DE); Florian Weber, Freising (DE)

(73) Assignee: MEDICAL INTELLIGENCE MEDIZINTECHNIK GMBH

( * ) Notice: Subject to any disclaimer, the term of this patent is extended or adjusted under 35 U.S.C. 154(b) by 448 days.

(21) Appl. No.: 16/205,295

(22) Filed: Nov. 30, 2018

(65) Prior Publication Data
US 2019/0168026 A1 Jun. 6, 2019

(30) Foreign Application Priority Data
Dec. 6, 2017 (EP) .................................... 17205741

(51) Int. Cl.
*A61N 5/10* (2006.01)
*H02J 9/06* (2006.01)
(Continued)

(52) U.S. Cl.
CPC ............ *A61N 5/1049* (2013.01); *A61B 90/16* (2016.02); *A61N 5/1067* (2013.01); *H02J 1/108* (2013.01); *H02J 9/061* (2013.01); *A61N 2005/1057* (2013.01); *A61N 2005/1074* (2013.01); *A61N 2005/1091* (2013.01); *A61N 2005/1094* (2013.01); *A61N 2005/1097* (2013.01); *H02J 1/082* (2020.01)

(58) Field of Classification Search
CPC ............ A61B 90/16; A61N 2005/1057; A61N 2005/1097; A61N 5/1049
See application file for complete search history.

(56) References Cited

U.S. PATENT DOCUMENTS 5,464,411 A 11/1995 Schulte et al.
8,088,003 B1 1/2012 Bickerton et al.
(Continued)

FOREIGN PATENT DOCUMENTS

WO 2013155632 A1 10/2013

OTHER PUBLICATIONS

European Patent Office, Extended European Search Report, Application No. 17205741.6, dated Apr. 20, 2018, 6 pages.

*Primary Examiner* — Christine H Matthews
(74) *Attorney, Agent, or Firm* — Quarles & Brady LLP (57) ABSTRACT

Controlling unit for a radiation source includes a mains-driven power supply terminal connectable to a mains-driven power supply, a battery-driven power supply terminal connectable to a battery-driven power supply, a failsafe power supply terminal, a processor unit to control the radiation source, and a patient-in-place sensor unit to provide a respective signal to the processor unit. The failsafe power supply terminal is connected to the mains-driven power supply terminal via a first diode and to the battery-driven power supply terminal via a second diode and he processor unit is connected to the failsafe power supply terminal to receive power from the higher voltage power supply terminal of the mains-driven power supply terminal and the battery-driven power supply terminal, respectively. The processor unit is adapted to shut down the radiation source in case a patient-not-in-place signal is provided.

16 Claims, 3 Drawing Sheets

(51) Int. Cl.
  *A61B 90/16* (2016.01)
  *H02J 1/10* (2006.01)
  *H02J 1/08* (2006.01)

(56) References Cited

U.S. PATENT DOCUMENTS

| | | |
|---|---|---|
| 8,100,132 B2 | 1/2012 | Markstroem |
| 8,393,821 B2 | 3/2013 | Wiberg et al. |
| 8,567,405 B2 | 10/2013 | Arn et al. |
| 2011/0036356 A1 | 2/2011 | Arn et al. |
| 2014/0265845 A1 | 9/2014 | Williams |

CRANIAL IMMOBILIZATION APPARATUS FOR RADIATION THERAPY

CROSS-REFERENCE TO RELATED APPLICATIONS

This application claims benefit of European Patent Application 17205741.6 filed Dec. 6, 2017, which is incorporated herein by reference in its entirety.

FIELD OF THE INVENTION

The present invention relates to a cranial immobilization apparatus for radiation therapy, in particular to a to a cranial immobilization apparatus for radiation therapy which provides an improved operation for a patient.

BACKGROUND OF THE INVENTION

One out of a plurality of cancer treatment options is applying radiation, in particular X-ray radiation to a patient's tumor region in order to destroy the tumor cells. However, as X-ray radiation itself does not distinguish between cancer cells and intact body cells of a human, it is desired that the radiation dose to healthy cells is minimized. For applying radiation, proper systems are available which provide a sufficient exact dosing and a sufficient exact focus of the radiation. However, it is important that the patient to be treated maintains in the predetermined position, which means the correct relative position with respect to the focus of the radiation source. In case a patient moves during treatment, there is a significant risk, that the radiation focus no longer corresponds to the cancerous cells or tumor, which does not only reduce the dose applied to the cancer tissue, but may further result in undesirable side-effects to the patient, in particular injuries to intact tissue adjacent to the cancerous cells or tumor.

To overcome this particular problem, there are different approaches in the prior art, relating to the fixation of the patient with respect to the radiation source. One common approach is to provide a mouthpiece, which is connected with the patient's teeth. If the mouthpiece fits with a patient-specific tooth pattern, the head position of the patient can be fixed. If the patient bites onto the mouthpiece, the patient's skull reaches a defined position with respect to the mouthpiece. Consequently, if the mouthpiece is in a predefined position with respect to the radiation source, the patient's skull will also be. Therefore, when treating the patient's head, in particular cancerous cells or a tumor in the patient's head, a defined position of the radiation source with respect to the patient's head or skull can be established. Such systems are known for example from U.S. Pat. Nos. 5,464,411, 8,393,821, 8,088,003, 8,567,405, 8,100,132 and US 2011/0036356.

There may be a need to further improve the possibility to detect whether the patient is indeed in the correct position, e.g. correctly fits the mouthpiece, and an adequate surveillance of the treatment setup, in order to better detect and react on failures in order to improve alignment of the radiation source with respect to the patient's head, in particular in relation to the cancerous cells and tumor at the patient's head.

Subject Matter of the Present Invention

The present invention provides a device and a method for controlling and monitoring a radiation treatment setup. In particular, the present invention provides a control unit for controlling a radiation source and monitoring the patient's position according to the independent claims, wherein further embodiments of the controlling unit are incorporated in the dependent claims.

According to an embodiment of the invention, a controlling unit is provided for controlling a radiation source to be connected for patient treatment, wherein the controlling unit comprises a mains-driven power supply terminal to which a mains-driven power supply is connectable; a battery-driven power supply terminal to which a battery-driven power supply is connectable; a failsafe power supply terminal; a processor unit being adapted for controlling the radiation source to be connected; a patient-in-place sensor unit being adapted to sense if a patient is not in place for treatment with the radiation source to be connected and to provide a respective signal to the processor unit; wherein the failsafe power supply terminal is connected to the mains-driven power supply terminal via a first diode and to the battery-driven power supply terminal via a second diode; wherein the processor unit is power supply-connected to the failsafe power supply terminal, so as to receive a power supply from the higher voltage power supply terminal of the mains-driven power supply terminal and the battery-driven power supply terminal, respectively; wherein the patient-in-place sensor unit is power supply-connected to the mains-driven power supply terminal, wherein the processor unit is adapted to shut down the radiation source to be connected if a patient-not-in-place signal by the patient-in-place sensor is detected.

Thus, a controlling unit can be provided, which has an improved failsafe build up which can be activated in the event that a mains power supply breaks down, for example owing to a fuse error, cable disruption or grid complications. In such circumstances it is desirable that a failure of the mains power supply can be detected and measures can be taken, even if the mains power supply is no longer available. On the other hand, when operating the controlling unit with a battery power supply only, this may lead to an early discharge of battery, which may lead to a failure of the controlling unit and high maintenance. For this purpose, the combination of the mains-driven power supply and a battery-driven power supply is used, where the battery power supply however is only charged with power consumption, if the mains power supply is not available. By providing respective terminals for connecting a mains power supply and a battery power supply, which terminals are connected via respective diodes to a failsafe power supply terminal of the controlling unit, it can be established, that the power consumption will be provided by the mains power supply as long as the mains power supply is available, and that the power supply is operated by the battery, only if the mains power supply is down. As a failure of the mains power supply could lead to a serious situation, the battery power supply shall only provide energy for the failsafe detection, but preferably not for power consumptive elements of the controlling unit. Therefore, for example a processor unit, which is advantageous for detecting a failure, should be connected to the failsafe power supply terminal having a backup from the battery power supply. This is also relevant, as the processor unit, in the event of mains power supply breakdown, should be able to shut down a radiation source in order to bring the controlling unit and the entire setup with the patient, e.g. the controlling unit and the radiation source, into a failsafe state. As an option, the patient-in-place sensor unit can be power supply connected to the mains-driven power supply terminal, as long as the sensing of the patient-in-place situation is failsafe. This is for example the case if both a loss of power of the patient-in-place sensor unit, as well as the detection that the patient is not in place results in the same signaling leading to a shutdown of the radiation source.

Patient treatment may include therapeutic measures like e.g. gamma or x-ray therapy, but may also include imaging like fluoroscopy or x-ray imaging, diagnosis like fluoroscopy or x-ray imaging based diagnosis, and positioning. The described device however are particularly relevant for those kinds of patient treatment where a misalignment may result in undesirable side-effects, which is e.g. the case for gamma or x-ray therapy.

According to an embodiment of the invention, the processor unit is further adapted to shut down the radiation source to be connected if a breakdown of the mains power supply to be connected occurs.

Thus, it can be guaranteed that the radiation source will be stopped from radiating if an unsafe operation is expected. This can be for example a breakdown of a mains power supply to be connected. If for example the patient-in-place sensor receives power from the mains power supply, if a breakdown of the mains power supply were to occur, it could lead to a situation where it cannot be detected that a patient is no longer in its exact defined position. For this purpose, the processor unit may be adapted to emit an interlock signal to a radiation source to be connected to disable the radiation. Further, the interlock signal may additionally activate an alerting system so as to give notice to an operator of the controlling unit, which may be for example a doctor or auxiliary personnel. It should be noted that the controlling unit according to the invention may be coupled to the radiation source via an optical signal transmission line in order to electrically decouple the controlling unit.

According to an embodiment of the invention, the controller unit further comprises a power breakdown sensing unit being adapted to sense a breakdown of the power supplied via the mains-driven power supply terminal, and to trigger the processor unit to shut down a radiation source to be connected in the event of breakdown of a mains power supply to be connected.

Thus, it is possible to directly sense the power or a breakdown of the power at the mains-driven power supply terminal and to provide a respective signal to the processor unit. The processor unit may then shut down the radiation source, for example by sending out an interlock signal to disable the radiation. It should be noted, that not only a breakdown but also any irregularity of the power supplied via the mains-driven power supply terminal may be detected.

The power breakdown sensing unit is adapted to sense a breakdown of the power supplied via the battery-driven power supply terminal.

Thus, although it is not very likely, a problematic power condition on the battery power supply site may be detected, so that even in this case, the radiation source can be shut down. It should be noted, that not only a breakdown but also any irregularity of the power supplied via the battery-driven power supply terminal may be detected.

According to an embodiment of the invention, the power breakdown sensing unit is integrated into the processor unit.

Thus, no separate element needs to be provided for the breakdown sensing. If a voltage meter or an ampere meter is provided in the respective power line, the signal of the ampere meter or the voltage meter can directly be provided to the processor unit having integrated the respective sensor unit to detect and evaluate the measurement signals in order to sense an irregularity or breakdown of the power supplied by either/or the mains power supply and/or the battery power supply.

According to an embodiment of the invention, the patient-in-place sensor unit is power supply connected to the mains-driven power supply terminal via an electrically independent switch, which can be operated by an operator of the controlling unit.

Thus, it is possible for an operator to mechanically switch on and off those components of a patient-in-place sensor which are power consumptive such as a vacuum pump, the function of which will be described later.

According to an embodiment of the invention, the patient-in-place sensor unit is adapted to release a patient-not-in-place signal upon loss of power of the patient-in-place sensor unit.

Thus, it can be guaranteed, that not only a situation can be detected where the patient is no longer in place, but also a situation, where the patient-in-place sensor unit is no longer provided with power. This setup may be used as a redundant detection to the breakdown sensor, e.g. a voltage or ampere meter, which is provided at the respective terminal as described above.

According to an embodiment of the invention, between the battery-driven power supply terminal and the first diode, a switch is provided which is driven into a closed position by a relay which is actuated by the processor unit upon triggering by an operator of the controlling unit.

Thus, an operator may trigger the operation of the controlling unit, and the processor unit actuates the power as long as the respective conditions are fulfilled. The operation may for example be interrupted by a trigger of the operator, for example when terminating the operation of the controlling unit in a planned manner.

According to an embodiment of the invention, the patient-in-place sensor unit comprises a pressure sensor sensing a pressure within a pump-driven vacuum lumen to be connected to the controlling unit, wherein the patient, when being in place, covers an opening of the vacuum lumen, so as to tighten the vacuum lumen. When not being in place the patient does not cover the opening, so that a resulting pressure change, e.g. a pressure drop can be sensed by the pressure sensor.

Thus, the correct position of a patient can be monitored by a part of the patient's body, which covers a vacuum lumen. As soon as the patient's body part leaves the respective covering position, this may automatically lead to a change of pressure within the vacuum lumen, so that a respective detected pressure change may be considered as an indicator that the patient is no longer in place.

According to an embodiment of the invention, the patient-in-place sensor unit comprises a vacuum pump, the pump-driven vacuum lumen and a mouthpiece having an individually adaptable patient dental pattern being adapted for positively fitted receiving of that patient's teeth, wherein the opening of the vacuum lumen is arranged in that it may be fixed to a patient's maxilla, in particular may be covered by the patient's palate, if the patient's teeth positively fit the patient dental pattern.

Thus, the mouthpiece construction, which is established for a proper positioning of the patient's head, can be directly combined with a detection, whether the patient is in a predefined fitted position with respect to the mouthpiece. The mouthpiece may be fixedly connected to the treatment apparatus, e.g. via an adaptable frame to a table, where the patient rests during treatment. As soon as the patient no longer bites onto the mouthpiece, the opening of the vacuum lumen may be released by the patient's maxilla or palate, so that the pressure within the vacuum lumen alters, e.g. the vacuum drops. The vacuum lumen may be, for example, evacuated by a vacuum pump, so that a release of the opening may lead to an increasing pressure, i.e. drop or breakdown of the vacuum, resulting in a respective signal, that the patient is no longer in place. With respect to this, if a patient-in-place signal is received, which means that the vacuum lumen of the mouthpiece is properly covered by the patient's maxilla or palate or alternatively other parts of the patient's mouth, this is a clear indication that the position of the patient's head is well defined with respect to the focal point of the radiation source. It should be noted that the mouthpiece with the opening may be arranged remote from the vacuum lumen. The vacuum lumen may for example be located in a housing of the controlling unit, whereas the lumen may have a tube connection to the mouth piece at the patient's site, so that the opening is remote from the lumen. Alternatively, the lumen may also be at the mouthpiece having the opening. In this case the pressure sensor may be remotely arranged in the housing of the controlling unit, as well as a vacuum pump to which the lumen is connected via a duct or tube. The lumen may also be arranged somewhere between the controlling unit and the mouthpiece. In this case there may be provided a duct or tube to both, the mouthpiece and the pressure sensor in controlling unit. The pressure sensor may also be arranged immediately adjacent the lumen. If the lumen is remote from the controlling unit, an additional signal line is required. This signal line may require measures to comply with electromagnetic compatibility (EMC).

According to an embodiment of the invention, the controlling unit further comprises a vacuum conduct selector to selectively connect the vacuum pump to the pump-driven vacuum lumen of the patient-in-place sensor unit and/or to a pump-driven patient positioning unit to be connected to the controlling unit.

Thus, the built-in pump of the controlling unit may not only be used for the patient-in-place sensor unit, but also for a patient positioning unit. This means that the controlling unit needs only a single pump for different purposes.

According to an embodiment of the invention, the controlling unit further comprises a patient positioning unit, wherein the patient positioning unit comprises a pump-driven vacuum cushion.

Thus, the positioning of the patient can be supported by the patient positioning unit. Although the patient positioning may be maintained by the mouthpiece, it may be much more convenient for a patient to rest on an adaptable patient positioning unit, which includes a vacuum-driven cushion or pillow. It should be noted that the patient positioning unit may be a device, which can be evacuated once, whilst maintaining its shape for patient positioning by closing a respective valve, so that a permanent pump operation is not necessary. With this respect, the pump then may be used for the patient-in-place sensor unit to provide a respective vacuum for the vacuum lumen. Nevertheless, the controlling unit may also be provided with two separate pumps, one for the patient positioning and one for the patient-in-place sensing.

According to an embodiment of the invention, the controlling unit further comprises a battery power supply being connected to the battery-driven power supply terminal and having a battery supply output voltage.

Thus, the controlling unit may directly be provided with a battery-driven power source, which may be provided within a housing of the controlling unit and may be portable.

According to an embodiment of the invention, the controlling unit further comprises a mains power supply being connected to the mains-driven power supply terminal and having a mains supply output voltage, wherein the mains supply voltage is higher than the battery supply voltage.

Thus, the controlling unity may be provided with an internal mains power supply, which is in a particular voltage relation to the battery power supply, so as to provide the power mainly by the mains power supply and gets the power from the battery power supply only if the mains power supply breaks down. It should be noted that the internal mains power supply of the controlling unit may also be realized as a separate power supply which may be detachably coupled to the controlling unit.

According to an embodiment of the invention, the controlling unit further comprises an alerting unit, wherein the processor unit is adapted to trigger the alerting unit in the event of breakdown or any irregularity of the mains power supply, wherein the alerting unit is adapted to give notice to an operator of the controlling unit.

Thus, it can be guaranteed, that the operator receives a respective notice that a failure occurred. In this case, the operator may crosscheck whether the control unit has reliably shut down the radiation source and may take care of the patient.

It should be noted, that the above described embodiments may be combined in order to gain a synergetic effect of such a combination without departing from the general concept of the invention.

BRIEF DESCRIPTION OF THE DRAWINGS

The above described and other aspects and properties of the above mentioned embodiments of the present invention will be described with respect and reference to the following drawings.

DETAILED DESCRIPTION OF EXEMPLARY EMBODIMENTS

In general, prior art controlling units for a patient-specific cranial immobilization may gain from the subject matter of the present invention when working with radiation sources, like a linear accelerator system (LINAC system). For example, a microprocessor may control alarming parts, vacuum sensors, and vacuum pumps during treatment. In the unlikely event a microprocessor goes wrong or the mains power cable is disconnected, the vacuum level may drop without prior warning. As a result, in particular for a head treatment, the patient's head may not be adequately fixed with, for example, a mouthpiece, under low vacuum level condition. Avoiding a head movement during radiotherapy then could lead to a better alignment which then may result in a more efficient patient treatment and therapy.

The electronic controlling system according to the invention, provides a solution for this aspect.

The controlling unit, also referred to as power controlling unit (PCU) may also be used for providing a desired vacuum to a mouthpiece to immobilize a patient's head during treatment, and a desired vacuum to sharpen a cushion/pillow with a patient's head during a patient setup phase. The PCU may also be used to monitor the vacuum pressure to ensure the vacuum at the mouthpiece to be always within a correct range and to activate an alarm if the vacuum at the mouthpiece is no longer in the correct range. Further, the PCU may activate the alarm in the event of internal failures.

The controlling unit according to the invention provides an effective solution by providing a separation between a control path of the microprocessor/processor unit and the control path of a vacuum pump. In this way, a vacuum pump may directly be powered via a mechanical switch being controlled by the operator, whereas a microprocessor can monitor the vacuum level without interrupting the vacuum pump. In addition, a battery backup and check electronic hardware may be used to activate the alarming system in the event of a mains power loss during the treatment. In order to save battery lifetime, such a battery backup and check electronic hardware can only be active and on hold when the vacuum pump is running, for example when using the pump to evacuate the patient positioning unit to immobilize the patient's head with the mouthpiece. If mains power is lost, for example due to a broken cable for whatever reason, during the treatment, the microprocessor/processor unit is still powered by the battery backup and check electronic hardware and further may detect such as power loss/irregularity and vacuum drop. The controlling unit may be adapted to immediately send a stop interlock signal to terminate a radiation source, in particular a LINAC beam, and may also activate the alarming system. The alarming system may be either a visible or an audible signal or a combination thereof, for example a flashing red lamp and a speaker. Any failure due to a microprocessor/processor unit, however, will not impact the vacuum level for a patient position/in place sensing and a patient positioning, for example, a patient's head immobilization, because the vacuum pump may be directly powered by the mains power via a mechanical switch. Therefore, the patient may still be in a safe condition at both failure scenarios.

Figure 1:
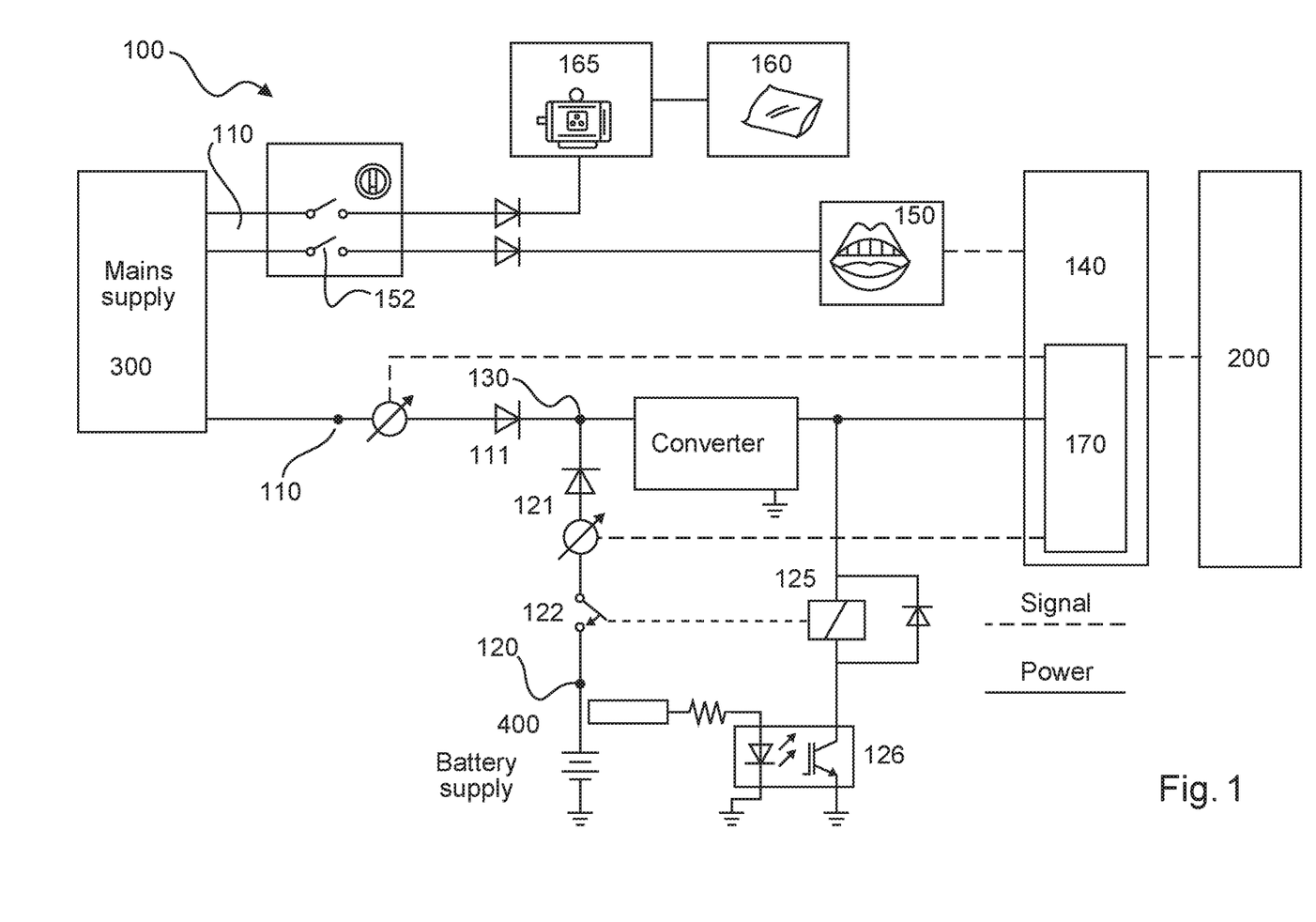
FIG. 1 is an exemplary set up of the controlling unit according to an embodiment of the invention.

FIG. 1 illustrates the general set up of such a controlling unit 100. The controlling unit 100 may include a mains-driven power supply terminal 110 to which a mains power supply 300 may be connected. The mains power supply 300 may be also part of the controlling unit 100, but may also be provided as a separate device. As can be seen from FIG. 1, the mains-driven power supply terminal 110 may be provided for different purposes. It should be noted that the mains power supply driven terminal 110 may be provided at different locations, as can be seen in FIG. 1. It should also be noted, that the voltage level of these different positions 110 is not mandatorily the same and may differ according to the needed and required voltage level of the respective units to be provided with power. The controlling unit 100 further comprises a battery-driven power supply terminal 120, to which an external battery power supply 400 may be connected. It should be noted that the battery power supply 400 may also be directly implemented into the controlling unit 100, but also may be an external device. The mains-driven power supply terminal 110 is connected to a failsafe power supply terminal 130 via a diode 111. In the same way, the battery-driven power supply terminal 120 is connected to the failsafe power supply terminal 130 via a diode 121. It should be noted that the voltage or the current at/through the mains-driven power supply terminal 110 as well as the battery-driven power supply terminal 120 may be detected and a respective detection signal may be provided to a power breakdown sensing unit 170. Further, it should be noted, that between the battery-driven power supply terminal 120 and the failsafe power supply terminal 130, there may be provided a switch 122 which may be operated by a relay 125. The relay 125 may be controlled by the processor unit 140, depending on various preset conditions. It should be noted, that the voltage or current can also be detected at other locations, insofar the detection is achieved. For example, if the detection is a current detection, the detection can also be conducted between the diodes 111, 121 and the failsafe power supply terminal.

The mains-driven power supply 300 may also be a power grid independent power supply, like a battery. The mains-driven power supply 300 alternatively may be a plug for a power grid connector, wherein the mains power supply 300 may include a transformer or a switch-mode power supply, a rectifier and a voltage regulator for supplying a desired voltage at the output of the mains power supply 300. As an alternative, the mains-driven power supply 300 may be a plug for a power adaptor, wherein the mains power supply 300 may include a voltage regulator and/or a rectifier for supplying a desired voltage at the output of the mains power supply 300. The power adapter may be transformer based or switch mode power supply.

The mains-driven power supply terminal 110 may be divided in case two or more different voltage levels are required from a mains-driven power supply 300. In case of corresponding voltage levels the mains-driven power supply terminal 110 may be a common terminal for the patient-in-place sensor unit 150 and the processor unit 140. Alternatively, in case of corresponding voltage levels the mains-driven power supply terminal 110 may be separated terminals for the patient-in-place sensor unit 150 and the processor unit 140, e.g. for reasons of potential separation or separate outlets from a housing. As this is of no relevance for the invention, the several terminals are all referred to as mains-driven power supply terminal 110 in FIG. 1 and FIG. 2.

The battery power supply 400 may include non-chargeable batteries, which increases the maintenance free period, as non-chargeable batteries usually have a lower internal loss. The battery power supply 400 however may also include chargeable batteries, which saves resources of battery material. The battery power supply 400 including chargeable batteries may be connected to the mains power supply 300 in order to permanently charge the chargeable battery or batteries.

The patient-not-in-place signal of the patient-in-place sensor unit 150 may be an explicit signal indicating that the patient is not in place. The patient-not-in-place signal may also be the absence of a signal indicating that a patient is in place. The latter is a dead fail safe arrangement, as a failure in the power supply for the patient-in-place unit 150 may also lead to an absence signal indicating a potential error in setup.

The failsafe power supply terminal 130 provides power to operate the processing unit, e.g. a microprocessor 140, so that the microprocessor may be provided with respective power from the mains power supply 300 as long as the mains power supply is available and in operation. However, if the mains power supply breaks down or has a malfunction, the microprocessor 140 may be provided with power through the battery supply 400 to be connected. The combination of the diodes 111 and 121 guarantees that if the mains power supply provides a higher voltage than the battery power supply, the power consumption may be taken from the mains power supply in order to save energy from the battery power supply. The voltage supplied at the failsafe power supply terminal 130 may be converted into a proper voltage range to provide the microprocessor or processing unit 140 with power. It should be noted that the voltage or current detecting which is the power breakdown sensing may be implemented within the processing unit 140. It should be noted that the sensing unit 170 does not only detect a full breakdown but may also detect any irregularity in the power supply of either the battery power supply or the mains power supply. If the processing unit 140 detects any malfunction from either the power supply branch or from a patient-in-place sensor unit 150, the processor unit 140 may provide a respective signal to a radiation source 200. This signal from the processor unit 140 to the radiation source 200 may be an interlock signal which may be sent to the radiation source. This may be an electrical signal, but may also be an optical signal. It should be noted that the signal from the processor unit 140 to the radiation source 200 may also be of any other physical conditions. The processor unit 140 may be provided with power from the failsafe terminal 130. However, this power supply is separated from the power supply of a vacuum system.

The vacuum system, for example, may include a vacuum pump for operating a patient-in-place sensor unit 150. The signal of the patient-in-place sensor unit 150 may then be sent to the processor unit 140 based on which the processor unit may detect a proper position of a patient or that a patient has left the correct position, so that in the event of any failure, the processor unit may shut down the radiation source 200. As can be seen from FIG. 1, the power supply of the vacuum pump or in general the patient-in-place sensing unit 150 or a patient positioning unit 160 may be provided via the mains-driven power supply terminal 110, which however is not covered by the back-up of the battery supply. The power may be switched by a respective switch 152, so that an operator, for example a doctor, physician or auxiliary personnel may interrupt or close the switch 152 to operate a pump 165 which operates a patient positioning unit 160.

The failsafe power circuit may also include the switch 122, which may be actuated by a relay 125. The relay may be activated by a semiconductor device 126 which may receive a triggering or activation signal from the processor unit 140 via an optical signal. This may sufficiently separate the circuits from each other.

Figure 2:
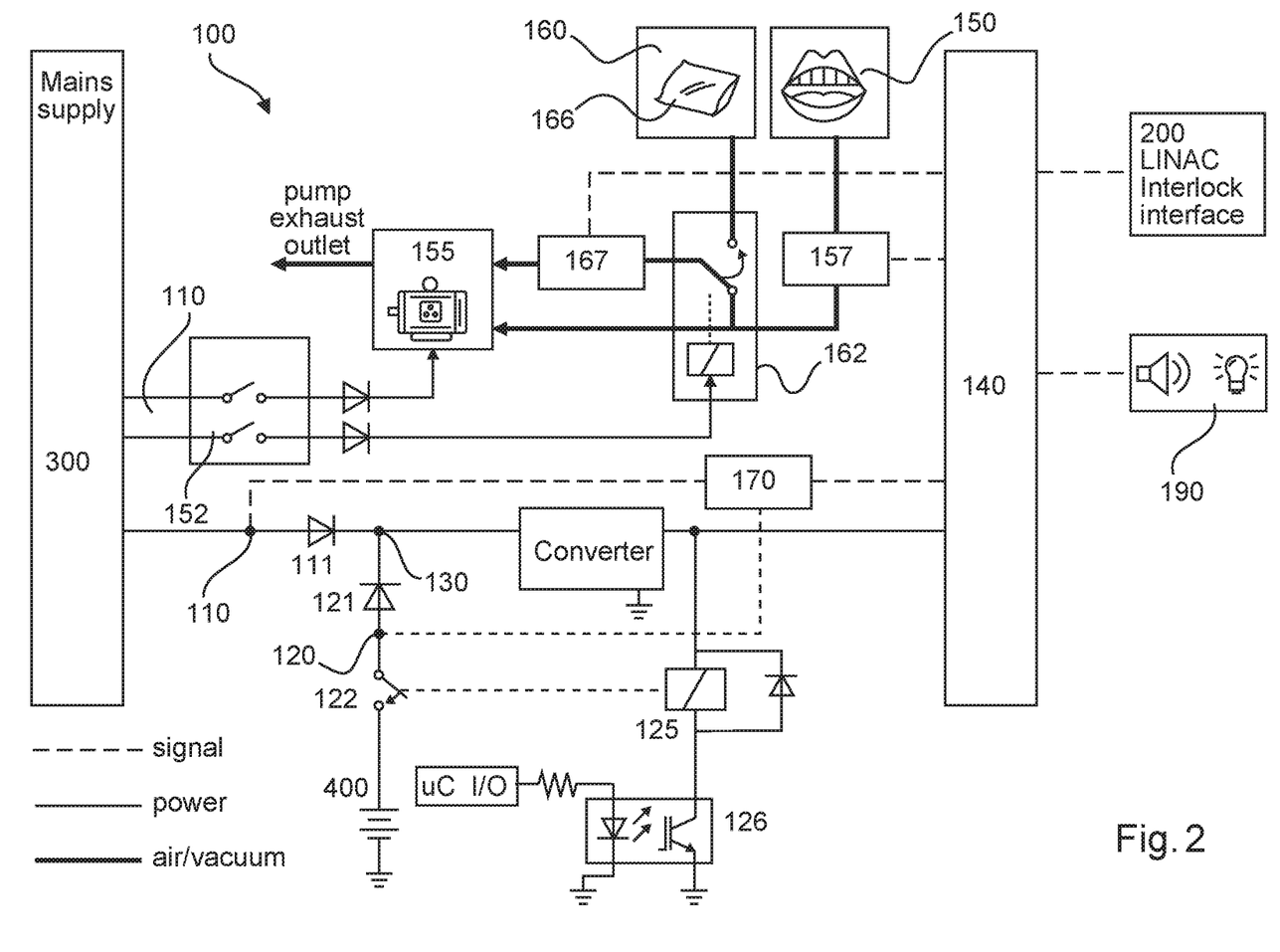
FIG. 2 is a further exemplary set up of the controlling unit according to an embodiment of the invention.

FIG. 2 illustrates a further embodiment of the controlling unit 100. Same references refer to likewise elements and will not completely repeated.

FIG. 2 illustrates not only the signal lines in dashed lines but also the power lines in solid lines, as well as vacuum lines in thick solid lines. The mains power supply 300 may be connected to a mains-driven power supply terminal 110. A battery 400 may be connected to a battery-driven power supply terminal 120. The mains-driven power supply terminal 110 may be connected to the failsafe power supply terminal 130 via the diode 111. Likewise, the battery-driven power supply terminal may be connected to the failsafe power supply terminal 130 via the diode 121. This setup provides the property that the energy consumption may take place via the higher voltage branch of the battery and mains power supply. As already described with respect to FIG. 1, the battery power supply line may include a switch 122 which may be activated by a relay 125. The relay may be activated by a semiconductor element 126 which may be controlled by an optical signal, which may be triggered by the processor unit 140. Thus, the processor unit 140 may maintain the battery power supply as long as the required conditions are fulfilled. As can be seen from FIG. 2, the power/voltage/current may be detected at the mains-driven power supply terminal as well as the battery-driven power supply terminal. The detecting may take place by means of the voltage meter or ampere meter, the signal of which may be provided to a power breakdown sensing unit 170. Although the power breakdown sensing unit 170 is shown as a separate unit, this unit may also be implemented in the processor unit 140, as illustrated in FIG. 1.

The mains-driven power supply terminal 110 may also feed a respective vacuum pump via the mechanical switch 152. If switch 152 is closed, pump 155 may be supplied with power. Further, via a separate switch which may also be included in switch 152, a vacuum selector 162 may be activated to selectively connect pump 155 to either a patient positioning unit 160 and a respective vacuum cushion 166 or to the patient-in-place sensor unit 150. The patient-in-place sensor unit 150 may also include a pressure sensor 157 which may detect a respective pressure in the patient-in-place sensor unit 150, details of which will be described with respect to FIG. 3 in the following. If the pressure sensor 157 detects a pressure drop or a pressure increase (depending on whether the lumen is a vacuum lumen or a pressure lumen), pressure sensor 157 may provide a signal to the processor unit 140. The processor unit 140 may evaluate the pressure situation as well as the power situation and may provide a respective shutdown signal to the radiation source 200. This signal may be an interlock signal which may be received by an interlock interface of the radiation source 200. The processor unit 140 at the same time may generate an alert signal, which may be an acoustic and/or an optical signal at the alerting unit 190. The patient positioning unit 160 may be provided with a vacuum cushion 166. This vacuum cushion or pillow 166 may be evacuated if the vacuum selector 162 connects the vacuum pump 155 to the vacuum cushion 166. If a cushion is evacuated once, the cushion can be closed by a respective valve, which is not shown, in order to maintain the shape of the vacuum cushion 166. If this has happened, the vacuum selector 162 may be switched into the in FIG. 2 down position in order to provide vacuum to the patient-in-place sensor unit 150. It should be noted that a further pressure sensor 167 may be provided to detect the pressure in the vacuum line to the pump 155. With this vacuum sensor, the vacuum in the vacuum cushion 166 may be sensed.

If the mains power supply breaks down, the vacuum is no longer provided to the patient-in-place sensor unit 150, so that it is possible that the patient is no longer in place (at least this cannot be detected any longer) and the focus of the radiation source may no longer be in the optimal position for treatment. However, as the processor unit 140 detects the voltage condition of the main power supply, the processor unit 140 may shut down the radiation source 200 upon detection of a failure in the mains power supply 300. If, however, there is any leakage in the vacuum system, this may lead to a change in pressure which may be detected by the pressure sensor 157. Even if the patient is correctly in place, this is a situation which cannot be fully monitored, so that the processor unit 140 may receive a respective signal from the pressure sensor 157 to shut down the radiation source. If, however, the processor unit 140 fails, it can be considered that both the vacuum for the patient positioning unit 160 is still in good order as well as the patient-in-place sensor unit 150. Therefore, in both error scenarios, it can be guaranteed that the patient will not suffer from misalignment of the radiation focus.

Figure 3:
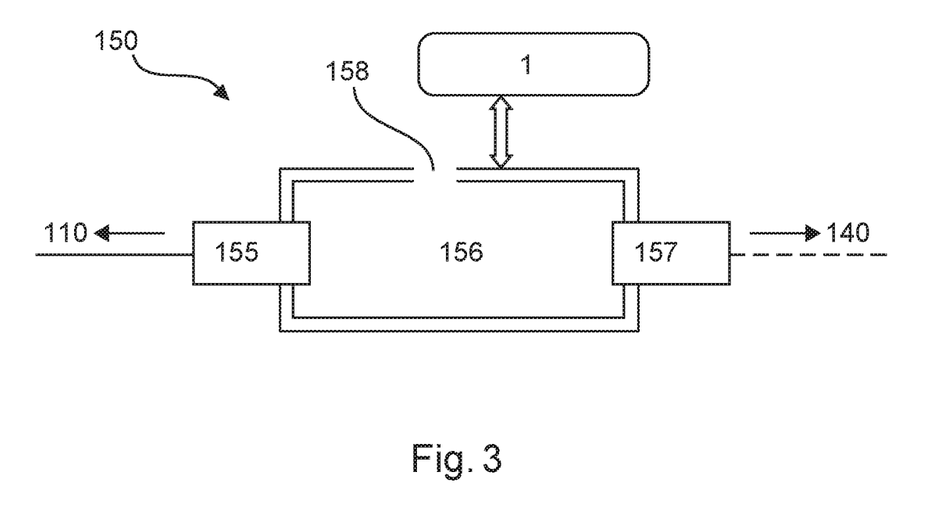
FIG. 3 is a schematic buildup of a patient-in-place sensor unit according to an embodiment of the invention.

FIG. 3 illustrates the general working principle of the patient-in-place sensor unit 150. The patient-in-place sensor unit 150 comprises a vacuum lumen 156 which is permanently evacuated by a vacuum pump 155. This vacuum pump 155 is power supplied via the mains-driven power supply terminal 110 illustrated in FIGS. 1 and 2. A pressure sensor 157 is provided to sense the pressure in the vacuum lumen 156. The vacuum sensor 157 is described with respect to FIGS. 1 and 2 and will not be repeated here. The sensor signal of the pressure sensor 157 may be provided to the processor unit 140. The vacuum lumen 156 has an opening 158. If the patient 1 covers with a part of his body the opening 158, the vacuum maintains in the vacuum lumen 156 as the vacuum pump 155 permanently evacuates the vacuum lumen 156. However, if the patient 1 moves, the opening 158 may be released, so that the pressure sensor 157 may detect a pressure increase or vacuum drop. This pressure increase may be signaled to the processor unit 140 in order to provide a base for shutting down the power of the radiation source 200. It should be noted that the lumen 156 may also be operated by (slight) pressure, which pressure level is maintained as long as the patient 1 covers the opening 158. In case the patient 1 moves the pressure drops which may be detected by pressure sensor 157.

The vacuum lumen 156 may be part of an entire system having a mouthpiece, wherein the mouthpiece is positioned in the patient's mouth. The fitting of the mouthpiece may be established by an individualized dental pattern which may be individually prepared in advance prior to patient treatment. This may allow that the patient's mouth fits the mouthpiece. In the event of a perfect fitting, e.g. the patient's palate as part of the patient, will cover the opening 158, so that the vacuum may be established in the lumen 156. If the patient opens his mouth, the palate may no longer cover the opening 158, so that the vacuum drops, which may result in a respective signal from the pressure sensor 157 to the processor unit 140. It should be noted that the lumen 156 can be provided directly in or at the mouth piece, as well as the pressure sensor 157. However, the pressure sensor may also be located remotely, e.g. in the controlling unit housing. In case the lumen 156 is in/at the mouth piece, the pressure sensor 157 is coupled to an air duct which is connected to the lumen 156. As an alternative, the lumen 156 is remote of the mouth piece, e.g. in the controlling unit housing. In this case the lumen is connected via an air duct to the mouth piece, which includes the opening 158. Release of the opening 158 then may lead to a vacuum drop in the lumen 156, even if the lumen 156 is remote from the mouth piece.

Although several modifications of the embodiments are described with respect to the figures, it should be understood that the alternatives may be combined. It should be noted that the particular combinations which are described with respect to the figures should not limit the scope of the invention.

The invention claimed is:

1. A controller for controlling a radiation source to be connected for patient treatment, the controller comprising:
    a mains-driven power supply terminal to which a mains-driven power supply is connectable;
    a battery-driven power supply terminal to which a battery-driven power supply is connectable;
    a failsafe power supply terminal;
    a processor being adapted for controlling the radiation source to be connected; and
    a patient-in-place sensor being adapted to sense if a patient is not in place for treatment with the radiation source to be connected and to provide a respective a patient-not-in-place signal to the processor;
    wherein the failsafe power supply terminal is connected to the mains-driven power supply terminal via a first diode and to the battery-driven power supply terminal via a second diode;
    wherein the processor is power supply connected to the failsafe power supply terminal, so as to receive a power supply from a higher voltage power supply terminal of the mains-driven power supply terminal and the battery-driven power supply terminal, respectively; and
    wherein the processor is adapted to shut down the radiation source to be connected and / or to trigger an alert signaller to be connected in case the patient-not-in-place signal of the patient-in-place sensor is detected.

2. The controller according to claim 1, wherein the patient-in-place sensor is power supply connected to the mains-driven power supply terminal.

3. The controller according to claim 1, wherein the processor is further adapted to shut down the radiation source to be connected in case of a breakdown of the mains-driven power supply to be connected.

4. The controller according to claim 1, further comprising a power breakdown sensor being adapted to sense an irregularity or a breakdown of the power supplied via the mains-driven power supply terminal, and to trigger the processor to shut down the radiation source to be connected in case of breakdown of the mains-driven power supply to be connected.

5. The controller according to claim 4, wherein the power breakdown sensor is adapted to sense an irregularity or a breakdown of the power supplied via the battery-driven power supply terminal.

6. The controller according to claim 4, wherein the power breakdown sensor is integrated into the processor.

7. The controller according to claim 1, wherein the patient-in-place sensor is power supply connected to the mains-driven power supply terminal via an electrically independent switch which can be operated by an operator of the controller.

8. The controller according to claim 1, wherein the patient-in-place sensor is adapted to release the patient-not-in-place signal upon loss of power of the patient-in-place sensor.

9. The controller according to claim 1, wherein between the battery-driven power supply terminal and the first diode a switch is provided, which can be driven into closed position by a relay actuated by the processor upon triggering by an operator of the controller.

10. The controller according to claim 1, wherein the patient-in-place sensor comprises a pressure sensor sensing a pressure within a pump driven vacuum lumen to be connected to the controller, wherein the pressure sensor is adapted to sense a pressure change when the patient is in place and covering an opening of the vacuum lumen, so as to tighten the vacuum lumen, and when the patient is not in place and not covering the opening.

11. The controller according to claim 10, wherein the patient-in-place sensor comprises a vacuum pump, the pump driven vacuum lumen and a mouth piece having an individually adaptable patient teeth pattern being adapted for positively fitted receiving of teeth of the patient, wherein the opening of the vacuum lumen is arranged in that it may be covered by a palate of the patient, if the teeth of the patient positively fit the patient teeth pattern.

12. The controller according to claim 11, further comprising a vacuum conduct selector to selectively connect the vacuum pump to the pump driven vacuum lumen and/or to a pump driven patient positioner to be connected to the controller.

13. The controller according to claim 1, further comprising a patient positioner, wherein the patient positioner comprises a pump driven vacuum cushion.

14. The controller according to claim 1, further comprising the battery-driven power supply being connected to the battery-driven power supply terminal and having a battery supply output voltage.

15. The controller according to claim 14, further comprising the mains-driven power supply being connected to the mains-driven power supply terminal and having a mains supply output voltage, wherein the mains supply voltage is higher than the battery supply voltage.

16. The controller according to claim 1, wherein the processor is adapted to trigger the alert signaller in case of breakdown of the mains-driven power supply, wherein the alert signaller is adapted to give notice to an operator of the controller.

* * * * *

UNITED STATES PATENT AND TRADEMARK OFFICE
CERTIFICATE OF CORRECTION

PATENT NO. : 11,185,716 B2
APPLICATION NO. : 16/205295
DATED : November 30, 2021
INVENTOR(S) : Rui Liu et al.

It is certified that error appears in the above-identified patent and that said Letters Patent is hereby corrected as shown below:

In the Claims

Column 12, Claim 11, Line 63, "is arranged in that" should be --is configured such that--.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*